United States Patent [19]

Volger et al.

[11] Patent Number: 5,093,131

[45] Date of Patent: Mar. 3, 1992

[54] REMEDY FOR TREATMENT OF SLEEP APNEA

[75] Inventors: Karl-Dieter Volger, Bickenbach; Werner Mohrke, Seeheim-Jugenheim, both of Fed. Rep. of Germany

[73] Assignee: Rohm Pharma GmbH, Weiterstadt, Fed. Rep. of Germany

[21] Appl. No.: 493,428

[22] Filed: Mar. 14, 1990

[30] Foreign Application Priority Data

Mar. 14, 1989 [DE] Fed. Rep. of Germany ....... 3908232

[51] Int. Cl.$^5$ .......................... A61K 9/20; A61K 9/28; A61K 31/535; A01N 43/42
[52] U.S. Cl. .................................. 424/464; 424/474; 514/233.2; 514/299; 514/651; 514/821

[58] Field of Search ................................ 424/464, 474; 514/233.2, 249, 253, 299, 651, 821

[56] References Cited

U.S. PATENT DOCUMENTS

4,157,394  6/1979  Fleckenstein et al. .............. 514/253

FOREIGN PATENT DOCUMENTS

2175206  5/1986  United Kingdom .

Primary Examiner—Thurman K. Page
Assistant Examiner—Carlos Azpuru
Attorney, Agent, or Firm—Oblon, Spivak, McClelland, Maier & Neustadt

[57] ABSTRACT

Sleep apnea is treated by administering a therapeutically effective amount of 2-isopropyl-2,8-bis(3,4-dimethoxyphenyl)-6-methyl-6-azaoctane nitrile to a subject.

5 Claims, No Drawings

REMEDY FOR TREATMENT OF SLEEP APNEA

BACKGROUND OF THE INVENTION

1. Field of the Invention

The present invention relates to a remedy for sleep apnea, i.e. nocturnal respiratory disorders. The therapy involves treatment of a subject with a composition containing 2-isopropyl-2,8-bis(3,4-dimethoxyphenyl)-6-methyl-6-azaoctane nitrile, preferably in the form of its pharmacologically approved acid addition salts (Verapamil), as the active ingredient.

2. Description of the Background

Recently, it has become known in medicine that a pathological condition diagnosed as sleep apnea represents a much more significant threat to a patient suffering from it than was previously generally assumed. Patients who suffer from sleep apnea have periods during sleep when they stop breathing, and these periods are interrupted by arousals. A constriction of the extrathoracic respiratory passages results in snoring and an inhibition of gas exchange.

As a rule, more than 100 phases per night are recorded in these cases, and, correspondingly, an apnea index of more than 10 per hour of sleep time. The length of the individual periods when respiration stops is generally more than 10 seconds.*)

*) A prevalence for an apnea index of 10 or more in 10% of the working middle-aged men is observed.

The psychophysical symptoms in sleep apnea are hypersomia, i.e. an excessively increased tendency to fall asleep during the day, and parallel to this, existing problems due to lack of continuous sleep such as performance slumps and depression. (cf. J. H. Peter, Die Erfassung der Schlafapnoe in der Inneren Medizin, Georg Thieme Verlag Stuttgart, 1987).

The leading symptom mentioned is heart failure. Other leading symptoms are arterial and pulmonary hypertension, as well as obesity and cardiac arrythmias during the night.

For therapy of sleep apnea in patients with high blood pressure, the anti-depressive protriptyline has been used, among other drugs [cf. E. C. Fletcher, R. D. DeBehnke, M. S. Lovoi, A. G. Gerin, Am. Intern. Med. 103, 190 (1985)]. Furthermore, there is a study concerning the influence of Nifedipine (1,4-dihydro-2,6-dimethyl-4-(2-nitrophenyl)-3,5-pyridine carboxylic acid dimethyl ester) on hypertension and apnea activity in sleep apnea syndrome. A significant reduction in blood pressure as well as in the number of apnea phases was achieved with this compound (cf. J. Mayer, D. Kunz, V. Koehler, J. H. Peter, T. Podszus, B. Steinbach, P. von Wichert, Z. Kardiol. 74, Suppl. 3, 34 (1985)).

In view of the known hazard of sleep apnea syndrome, which is now recognized by the medical community, the scope is not only to give the practicing physician effective remedies for treatment of this illness, but also, if possible, to provide a positive influence on the pathological conditions related to sleep apnea syndrome, i.e. conditions which cause it.

SUMMARY OF THE INVENTION

Accordingly, one object of the present invention is to provide a method of effectively treating sleep apnea.

Briefly, these objects and other objects of the present invention as hereinafter will become more readily apparent can be attained in a method of treating sleep apnea by administering to a subject suffering from the disorder a therapeutically effective quantity of 2-isopropyl-2,8-bis(3,4-dimethoxyphenyl)-6-methyl-6-azaoctane nitrile.

DETAILED DESCRIPTION OF THE PREFERRED EMBODIMENTS

The discovery of the present invention is that pharmaceutical substances which contain 2-isopropyl-2,8-bis(3,4-dimethoxyphenyl)-6-methyl-6-azaoctane nitrile (Verapamil), as the sole active substance or in combination with other effect-reinforcing or supplementing substances, is very effective in the treatment of sleep apnea syndrome. The active substance Verapamil has been known for a long time. Verapamil can serve as the prototype of a "calcium antagonist," a class of substances which were used with great success in the treatment of coronary diseases (cf. K. Lossnitzer, G. Pfennigsdorf and H. Braeuer, "Myokard, Calcium", Knoll A. G., Ludwigshafen 1983). Further, a combination of Verapamil and Triamterene (U.S. Pat. No. 4,157,394) and a combination of Verapamil, Triamterene and Hydrochlorothiazide has been found to be useful in the treatment of high blood pressure (DE-A 35 17 820; E. Mutschler Hrsg., Verapamil-Diuretika-Kombination, Wissenschaftliche Verlagsgesellschaft, Stuttgart, 1988).

Preferably, the active substance 2-isopropyl-2,8-bis(3,4-dimethoxyphenyl)-6-methyl-6-azaoctane nitrile (Verapamil) is used in the form of its pharmacologically acceptable acid addition compounds. Suitable pharmacologically acceptable acid addition compounds include, for example, the salts of d-tartaric acid, maleic acid, fumaric acid, succinic acid, citric acid, cinnamic acid, salicylic acid, adipinic acid, acetic acid, propionic acid, p-aminobenzoic acid, methanesulfonic acid, sulfuric acid, phosphoric acid, especially the hydrochlorides and lactates.

The dosage of Verapamil varies according to the severity of the sleep apnea syndrome, the age and the general disposition of the patient. In general, the daily dose of Verapamil is within the range of 0.5 to 12 mg/kg.

The pharmaceutical preparations of the present invention can be used parenterally and enterally. The preparation can be produced in the usual manner and can contain a conventional carrier and auxiliary substances or solvents.

Suitable embodiments of the preparations include solid preparations intended for oral administration such as tablets, capsules, coated tablets, and the like. For oral application, pharmaceutically acceptable solids such as mannitol, lactose, and others can be used as carrier materials.

Suitable binders for preparations include polyvinyl pyrrolidone, gelatin and cellulose derivatives. Additional additives include tablet fillers such as starch or alginic acid, lubricants such as stearic acid or its salts, and inorganic lubricants such as talc and colloidal silicic acid, as well as flavor correctants.

The active substances can be mixed with auxiliary substances in the usual manner, and granulated wet or dry. Depending on the types of additives used, a powder which can be shaped into tablets directly can also be obtained, if possible. The granulate or powder can be filled directly into capsules, or it can be compressed to form tablet cores in the usual manner.

Administration by means of ampoules and suppositories is also possible.

In a preferred embodiment, the active substance Verapamil is used in combination with the active substance 2,4,7-triamino-6-phenyl-pteridine (Triamterene). Preferably, the corresponding pharmaceutical preparations contain Verapamil-HCl and Triamterene in a weight ratio of 1:5 to 1:0.15, preferably in a weight ratio of 1:0.3125.

Having now generally described this invention, a further understanding can be obtained by reference to certain specific examples which are provided herein for purposes of illustration only and are not intended to be limiting unless otherwise specified.

The following is an example of a pharmaceutical preparation for therapy of sleep apnea, which contains Verapamil and Triamterene as active substances.

For the production of tablets, the active substances are mixed with a carrier and/or auxiliary substances in such amounts, in a tumbling mixer, that after compression, each tablet has the following composition:

100.0 mg Triamterene
80.0 mg Verapamil (hydrochloride)
100.0 mg lactose
10.0 mg talc
5.0 mg aerosil
10.0 mg magnesium stearate
10.0 mg corn starch Therapy with preparations which contain not only Verapamil and possibly Triamterene, but also a saluretic, is an especially preferred aspect of the invention. (Saluretics in the sense of the present invention cf. Ullmann's Encyclopedia of Industrial Chemistry 5th Ed., Vol. A9, 29-36 VCH, Weinheim 1987). A particularly acceptable saluretic is a benzothiadiazine derivative, especially 6-chloro-3,4-dihydro-7sulfamoyl-2H-1,2,4-benzothiadiazine-1,1-dioxide (hydrochlorothiazide). Preferably, the combination of the three active substances as a component of a dosage unit, preferably a film tablet, is in a weight ratio of Verapamil HCl to Triamterene to Hydrochlorothiazide of 16:5:2.5, especially preferably in a ratio of 160 mg:50 mg:25 mg. This makes a dosage available which contains 160 mg Verapamil HCl, 50 mg Triamterene and 50 mg hydrochlorothiazide [sic] in the form of a film tablet, as a daily dose. In addition, administration in capsule or coated tablet form is also possible.

The production of film tablets which contain the combination of active substances according to the invention can be undertaken as follows:

It is practical to carry out the production of film tablets in several segments:

A. Production of Verapamil granulate (60.4% Verapamil hydrochloride)

For the production of 100 kg Verapamil granulate, the following are required:

| | |
|---|---|
| Verapamil hydrochloride | 60.38 kg |
| ® Aerosil pyrogenic silicic acid | 0.51 kg |
| microcrystalline cellulose (® Avicel PH 102) | 19.10 kg |
| calcium carboxymethyl cellulose | 5.00 kg |
| (® Emcompress) tabletting aid calcium hydrogen phosphate dihydrate | 10.00 kg |
| magnesium stearate | 1.51 kg |
| talc | 3.50 kg |

Verapamil hydrochloride, ®Aerosil, ®Avicel PH 102, calcium carboxymethyl cellulose as well as ®Emcompress and talc are mixed in a mixer (Lueddige mixer FKM 130) for 5 minutes per blade cross, screened with a mesh width of 0.9 mm and then magnesium stearate is added. This material is mixed for another 10 minutes with the blade cross, and then compacted on a compactor.

At roller setting 9, material metering screw 8-9, the mass is compacted on the Hutt compactor under roller pressure of 70-80 KN. This results in a temperature of approximately 35° C. of the compactate. Subsequently, the material is granulated having a granulation screen with a mesh width of 0.9 mm. The granulate then demonstrates relatively good flow capacity in the flow test: 4-8 sec. Flow-through sample: 7-8 mm. The bulk density of the product was 6.3-6.9 g/ml. It had a Verapamil content of 60.38% which was 97.2-103.5% of the theoretical value.

B. Production of a Triamterene-Hydrochlorothiazide tablet mass

For the production of a tablet according to C, the following formulation is used (50 kg batch):

| | |
|---|---|
| Triamterene | 12.500 kg |
| Hydrochlorothiazide | 6.250 kg |
| calcium carbonate | 1.860 kg |
| pyrogenic silicic acid (® Aerosil [sic] | 0.410 kg |
| corn starch | 2.660 kg |
| lactose K | 2.160 kg |
| lactose granulate | 13.200 kg |
| polyvinyl pyrrolidone (average molecular weight 25,000) | 0.390 kg |
| magnesium stearate | 0.550 kg |
| microcrystalline cellulose | 4.820 kg |
| carboxymethyl starch | 1.000 kg |
| talc | 4.200 kg |
| | 50.000 kg |

C. Production of a Triamterene-Hydrochlorothiazide-Verapamil-HCl tablet (ratio 50 mg:25 mg:160 mg)

The Verapamil granulate A and the tablet mass B are sifted in the ratio stated and mixed in a Roehnrad mixer for 15 minutes. Subsequently, the mixture is facetted on an indexing tablet press with a die diameter of 10 mm and with a breaking notch, at 35 revolutions per minute and a compression pressure of 8-10 KN. Tablets with a weight of 465 mg are obtained.

D. Production of the film coating

The following formulation is used: For the coating, the following are required for a 249 kg batch:

| | |
|---|---|
| Veratide, tablets | 249.00 kg |
| water, purified | 8.400 kg |
| Eudragit RL 30 D | 2.660-4.980 kg |
| Eudragit RS 30 D | 0.658-1.245 kg |
| talc | 0.498-0.934 kg |
| triethyl citrate | 0.198-0.375 kg |
| simethicone emulsion | 0.000-0.003 kg |

1. The water is placed into a suitable VA pot and the triethyl citrate, the talc and the simethicone emulsion are worked in using the Ultra-Turrax.
2. The Eudragit dispersions RL 30 D and RS 30 D are placed into another VA pot, the solution from step 1 is allowed to run into the mixed dispersions and the resultant liquid is stirred with a compressed air stirrer.
3. Coating of the tablets is carried out according to the generally used principles of coating (K. Lehman and D. Dreher: "Anwendung Waessriger Kunststoffdispersionen zum Ueberziehen von Arzneiformen", Pharma. Ind. 34, 894–899 (1972); see appendix). A coating which covers the taste and decomposes rapidly is obtained.

Advantageous Effects

The use of the active substance Verapamil as the sole therapeutic principle or preferably in the combinations explained above permits effective therapy of sleep apnea. With this therapy, it is possible to reduce the apnea index of a subject into the normal range. At the same time, it can be assumed that harmful side effects, if any, occur to only a very minor degree. Further, there are also positive therapeutic effects for existing arterial and pulmonary hypertension.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of treating sleep apnea, comprising: parenterally or enterally administering to a subject a therapeutically effective amount of 2-isopropyl-2,8-bis(3,4-dimethoxyphenyl)-6-methyl-6-azaoctane nitrile.
2. The method of claim 1, wherein the active substance is in the form of a hydrochloride.
3. The method of claim 1, wherein the active nitrile compound is administered in combination with 2,4,7-triamino-6-phenyl pteridine.
4. The method of claims 1, 2 or 3, wherein the therapeutically active substance is administered in combination with 6-chloro-3,4-dihydro-7-sulfamoyl-2H-1,2,4-benzothiadiazine-1,1-dioxide.
5. The method of claim 1, wherein the therapeutically active nitrile compound is administered in a dose of 0.5 to 12 mg/kg.

* * * * *